United States Patent [19]

Young et al.

[11] Patent Number: 4,467,792
[45] Date of Patent: Aug. 28, 1984

[54] FRACTURE CAST BRACES

[75] Inventors: David E. Young, Watlington; David H. Boyes, Liverpool, both of England

[73] Assignee: Protectair Limited, Watlington, England

[21] Appl. No.: 458,178

[22] Filed: Jan. 17, 1983

[30] Foreign Application Priority Data

Nov. 18, 1982 [GB] United Kingdom ............... 8232996

[51] Int. Cl.³ .............................................. A61F 5/00
[52] U.S. Cl. .................................................. 128/88
[58] Field of Search ................... 128/88, 80 F, 80 C, 128/165, 90, 91 R; 3/22, 17; 2/22, 24

[56] References Cited

U.S. PATENT DOCUMENTS 4,249,524  2/1981  Anderson .............................. 128/88
4,337,764  7/1982  Lerman ............................. 128/80 F Primary Examiner—John D. Yasko
Attorney, Agent, or Firm—James & Franklin

[57] ABSTRACT

The head plate has a rectangular body with a central portion. The connecting portion of the flexible hinge part is integral with the central portion or the central portion is provided with a recess or slot into which the connecting portion is received. The upper and lower surfaces of the central portion of the body are substantially continuous and uninterrupted so as to provide maximum surface area for bonding to the casting material layers. The upper and lower surfaces may be provided with teeth or splines to increase the area of the bonding surfaces.

31 Claims, 5 Drawing Figures

FRACTURE CAST BRACES

This invention relates to fracture cast braces or hinge braces and to casts incorporating such braces.

Plaster of Paris is commonly used to form rigid casts, such as full leg casts, or casts which are applied to other areas, when immobilization of fractured bone, or bone required to fixate by virtue of elective surgery, is required. Such casts insure that fractured ends of bone, once "set" or re-aligned so that they approximate closely, do not undergo relative motion or displacement.

There are, however, therapeutic consequences to the use of plaster casts on long bones, not to mention certain inherent disadvantages of Plaster of Paris itself. Problems can be particularly pronounced when full leg casts are used on the long bones of the leg.

Commonly, orthopaedic surgeons and plaster technicians apply the cast not only to the affected part of the limb, but also to the adjacent (proximal or distal) part, e.g. the full leg or full arm cast. This is to ensure that most of the compressive load is transmitted from points beyond to points before the fracture. Perhaps even more important is the prevention of rotation which, if unchecked, could cause further damage at the fracture site, perhaps culminating in non-union of it.

Casts also provide general mechanical protection and their very nature encourages the patient to "guard" the injury.

When the whole leg is immobilized in a plaster cast for, say, a mid-shaft fracture of the femur, restriction of movement may continue for several months until healing is complete. Joint stiffness, together with considerable wastage of muscle under the plaster is common. In the wake of this, there is considerable need for physiotherapy and rehabilitative services which constitute a drain on health care resources. Disturbances of gait and delayed return to work, school, or other occupation are all additional sequels. To a lesser extent, some of these consequences occur when the long bones of the arm are immobilized for a long period and it is worth mentioning the delay in return to car driving which is often associated with the extended application of a rigid cast.

Recognition and awareness of these problems have made orthopaedic surgeons and plaster technicians receptive to methods which have the benefits of plaster casting, but with a reduction in the undesirable side effects. A major contribution to this aim has been the concept of cast-bracing which is otherwise called hinge-bracing or fracture-bracing.

This concept involves the application of two casts to long bones either side of a joint, e.g. above and below the knee or above and below the elbow. The two casts are jointed, at the time they are formed, by hinges, carefully applied so that the hinge axis lies along the condylar axis of the joint, the top and bottom of each hinge being embedded in the plaster cast.

Since the 1960's, the gradual development of the concept of ambulatory care of lower extremity fractures has progressed to the point where cast-bracing is now almost universally approved and accepted. The hinged cast has the fundamental advantage of allowing early motion in a joint. Furthermore, in the case of distal femur and upper tibial fractures, there is the advantage of early ambulation in addition to maintaining motion at the knee. Moreover, rotation is controlled.

Cast-bracing allows partial weight bearing at the fracture itself which promotes healing and mobilizes oedema fluid which would otherwise accumulate in the capsular and ligamentous structures of the joints. This is important since such accumulation leads to joint stiffness and temporary (sometimes permanent) loss of function.

The basic concept of cast-bracing or hinge-bracing is that immobilization is unphysiologic, while mobilization is always physiologic. The solutions of the cast-brace are thus physiological solutions.

Cast-braces in common use fall into two main categories:

a. Metal monocentric hinges:

These are usually made of aluminum or aluminum alloy and the upper and lower components are hinged together in a conventional manner about a single axis, the form of the actual hinge being of the bar and disc type. At the top and bottom of each component is a plate which is secured to the bar. This type of hinge allows no possibility of medial or lateral movement at the joint it is bracing. Elevation and depression of the distal part of the limb relative to the proximal part about a single axis is the only type of movement which this hinge allows for—hence, the name "monocentric." Clearly, very accurate position of both medial and lateral hinge axes on the elevation/depression axis of the joint is very important, otherwise these movements will be very difficult and torsional forces may be brought to bear on the affected limb. Fixation can only be correctly carried out by using a jig to ensure the centers of rotation of both hinges lie on the same axis and that they are in the same sagittal plane.

b. Polycentric plastic hinges:

These provide hinging by virtue of the property of maintained flexibility during repeated flexing and relaxing of modern polymer plastics including high molecular weight polyethylene. This is enhanced by the shaping of the single hinge component into broad convolutions parallel to the axis of elevation/depression of the limb and at right angles to the axis of the limb itself. Flexure of the hinge component may occur at any of these convolutions—hence, the hinge is termed "polycentric."

It is a feature of this type of hinge that on flexure, reactive forces build up within it, so that the musculature of the limb derives benefit from isometric exercises against the hinge. During walking, this effect also manifests as a gentle "throwing forward" of the leg which assists the patient in assuming a more normal gait despite having to wear the plaster cast. Because repeated flexure of plastic will eventually lead to fatigue of the material, plastic cast-braces are intended to be discarded after single use. At the top and bottom of each hinge are head-plates very similar (sometimes identical) to those used on monocentric bracing hinges. They are usually pressed from thin plastic sheet into rectangular plates with rounded corners, typically they have four holes about 1 cm in diameter, pressed through them in a regular pattern. These plates are usually rivetted to the inner aspect of the hinge which has a flattened end formed and drilled for the purpose.

It is accepted as axiomatic by the professionals who use and fit hinge-braces that there must be good contact between the Plaster of Paris and the plates on the hinge.

The holes in the plates enable wet plaster bandage to be pushed into them, so making contact with the bandage previously applied and improving lamination and bonding-in of the hinge plate. Even so, it is not always possible to achieve good lamination because the hinge component rises significantly from the plate and it is very difficult to eliminate dead space under the portion of the bandage adjacent to the hinge.

Plaster of Paris has a number of inherent disadvantages as a material for making casts and these disadvantages are well recognized. The setting time can be as much as 36 hours and patients may have to be hospitalized during this period. These casts are heavy and uncomfortable for the patient to wear. The casts are opaque to X-rays, hence, the progress towards healing cannot be monitored through the cast when Plaster of Paris is used.

These factors were probably the main motivation behind the development of the modern casting materials, including those marketed as "Baycast," "Orthoplast," "Hexcelite," "Zoroc," "Scotchcast," and "Litecast."

Most of these materials set quickly to load-bearing (in come cases as little as 20 minutes) and are radio-apparent as well as being very much lighter than Plaster of Paris.

"Baycast," for instance, is a polyurethane/polyol resin system impregnated onto a woven fabric with threads measured at 0.5 mm across and 0.25 mm down, enclosing interstices of 1.00 mm by 0.5 mm. The fabric usually has very little elasticity.

The resin curing period is accelerated by water, moisture in the air being usually sufficient to promote initial setting in about six minutes. The cured bandage is thin but very strong in the same plane as the weave. Strength increases rapidly as successive layers are built up, but it is essential, as with all casting materials, that good lamination is achieved between layers. This means there must be continuous contact between them.

Unfortunately, the failure to achieve excellent lamination when using the new casting materials in conjunction with hinge-braces has limited acceptance of this combination. Despite instructions by the manufacturers to bind the braces into the cast well down onto the hinged component past the head-plate, delamination and loosening of the braces is quite common. This is a potentially disastrous situation if the fractured limb suddenly becomes loaded.

There are several reasons for this problem of hinge/bond failure. Firstly, the fabric or base material of the new casting materials is not generally amenable to the "push-through" approach to the holes in the head-plate of the brace which is used with the soft bandage of the Plaster of Paris casting technique. Consequently, the holes simply represent lost bonding area.

Pressing the bandage against the holes in the head-plate to form a "dimple" which engages with the holes to some extent on setting, is probably acceptable on the lateral aspect of the limb, but on the medial aspect, there is an associated risk of nerve compression. This leads many users to eschew the practice. In any case, there is always a risk of using too much pressure and deforming the cast inwards. This could cause impingement on the limb and consequent skin abrasion.

Secondly, the significantly raised area of the head plate at and adjacent to the portion thereof where the hinge part joins the head plate causes a dead space under the bandage. The dead space significantly reduces the lamination surface area between the layers of casting material and the head-plate. The use of rivets to secure the head plate to the brace intensifies the problem since the rivets form excrescences on both faces, which, though small, still "lift" the bandage slightly away from the faces.

The combined effect of the holes in the plate and the dead space close to the hinge and around the rivets probably represent together loss of over 40% of the bonding area on the outside face and about 20% on the inner face. It should be borne in mind that these bandage or bracing materials have little conformability to tight radius curves, but this is precisely what current hinge/head-plate designs impose.

Finally, it must be stated that the actual bonding occurs between smooth polyethylene (the usual headpiece material) and the polyester resin used in Scotch-type materials and the polyurethane system of Baycast is *virtually nil.*

It is hardly surprising, then, that there have been less than totally satisfactory results with modern casting materials in hinge-bracing when the underlying design of current hinge-braces is considered.

It is, therefore, an object of the present invention to provide an improved hinge-brace for fracture casts, and one which is particularly suitable for use with modern resin casting materials.

In accordance with one aspect of the present invention, a hinge brace for use in a fracture cast is provided. The brace comprises a flexible hinge part having a head plate integrally formed on one end thereof. The head plate comprises a body with a central portion having substantially continuous, uninterrupted upper and lower surfaces. The upper and lower surfaces of the central portion are substantially coplanar with the adjacent surfaces of the hinge part, respectively. The head plate has a substantially arcuate cross-section. Peripheral sections of the body, located on either side of the central portion, are thinner than the central portion.

In accordance with a second aspect of the present invention, a head plate adapted to bond to casting material is provided for use in conjunction with a flexible hinge part having a connecting portion to form a fracture cast. The head plate comprises a body with upper and lower surfaces. The body includes a central portion with a recess of substantially the same dimensions as the hinge part connecting portion. The recess opens on one of said upper and lower surfaces. The recess is adapted to receive the connecting portion therein with the exposed surface of the connecting portion substantially coplanar with the body surface on which the recess opens. Thus, a substantially continuous and uninterrupted bonding surface is formed in the central portion of the body.

In accordance with another aspect of the present invention, a head plate is provided which is adapted for use in conjunction with a flexible hinge part having a connecting portion to form a hinge brace for a fracture cast. The head plate comprises a body having a central portion with substantially continuous uninterrupted upper and lower surfaces and a side portion. A slot is formed in the central portion, within the interior of the body, which opens at the side portion. The slot is of substantially the same dimensions as the connecting portion and is adapted to receive same therein.

Means are provided for affixing the connecting portion of the hinge part within the recess. The affixing means may comprise means extending from the recess and an opening in the connecting portion into which the extending means is received.

The body of the head plate preferably has an arcuate cross-section. Moreover, the body may have a peripheral section, on either side of the central portion, which is thinner than the central portion.

To enhance bonding, the body of the head plate may include one or more openings, spaced from the central portion, which extend from the lower surface to the upper surface. Moreover, the surfaces may be roughened or comprise teeth or splines. The teeth or splines may be divided into sets which contain teeth or splines extending in different directions.

The brace has a polycentric hinge portion secured at least at one end to a head plate for incorporation into a fracture cast. The head plate is preferably crescent-shaped in cross-section so as to conform approximately to the outer curvature of a limb. The end of the hinge portion is recessed in a substantially flush manner in the head plate.

The brace preferably has a head plate at each end of the polycentric hinge portion and, in the case where the headplates and hinge portion are integral, as by being moulded in one piece, the thickness of the central portion of the head plate is equal to that of the end of the hinge portion. Alternatively, the hinge portion is recessed in to the central portion of the head plate. In this case, it is preferred that the ends of the hinge portion are tapered slightly. The head plates have crescent-shaped cross-sections which, at their thickest points, are preferably about 25% to 30% thinner than rivetted hinge-to-head-plate thickness in conventional designs. At their thinnest points (along the edges), they have a thickness similar to existing braces. In one embodiment, the inner face of the head plate has a moulded recess exactly matching the dimensions of the hinge portion. Two stakes or protrusions are provided to engage holes in the hinge. These stakes or protrusions form spin-welds when pressed firmly with a suitable spinning glass or metal die. The excrescence on the inner hinge is minimal and less than a rivet.

Experiments on a "standard leg" and "standard arm" made from lengths of 6" and 4" heavy duty plastic soil-pipe, respectively, show that the present brace provides much better laminating surfaces than previously proposed braces as measured by increased bond strength and by other tests. Performance may be enhanced by the provision in the head plates of short narrow-angle splines or pegs which may be incorporated to face various impressed or reactive force directions.

It is possible to use the present hinge brace with Plaster of Paris since, with this material, too, lamination is improved.

To these and such other objects as may hereinafter appear, the present invention relates to fracture cast braces and, more particularly, to a head plate for a hinge brace for a fracture cast, as described in the following specification and recited in the annexed claims, taken together with the accompanying drawings, wherein like numerals refer to like parts, and in which:

Figure 1:
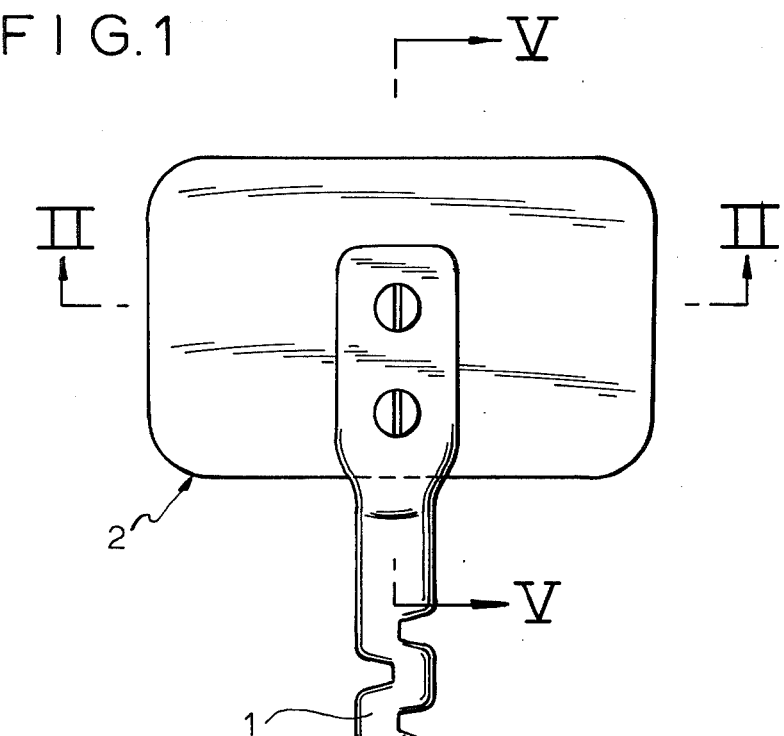
FIG. 1 is a plan view of a hinge brace showing various modifications.

Referring now to FIG. 1, there is shown a hinge-brace for a fracture cast. The brace comprises a polycentric hinge portion 1 which may, for example, be made of polyethylene and can be moulded or formed from polyethylene bar. At each end, the hinge portion 1 is secured to a head plate 2 and various head plate modifications and methods of securing are shown in the drawings.

The bottom half of FIG. 1 shows a head plate 2, integrally moulded with the hinge portion 1 while the upper half of FIG. 1 shows a separately made head plate subsequently secured to the hinge portion.

Figure 5:
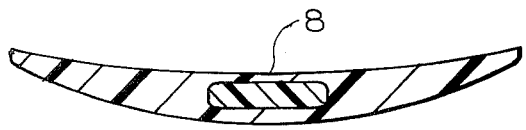
FIG. 5 is a view similar to FIG. 3 of a further modification.

The hinge portion 1 is of generally conventional shape and may have its major portion displaced out of the plane of the paper to prevent the brace, when in use, from rubbing against the condyles of a joint, (c.f. FIG. 5).

The head plate 2, however, differs considerably from the head plates of previously used hinge braces. As clearly shown in FIGS. 2, 3, and 5, the head plate 2 is crescent-shaped or arcuate in cross-section, being thicker in its central portion and thinner at the periphery. Furthermore, the head plate and hinge portion are secured together in a substantially flush manner so as to form continuous, uninterrupted bonding surfaces to avoid the possibility of a dead space forming when the brace is used.

Figure 2:
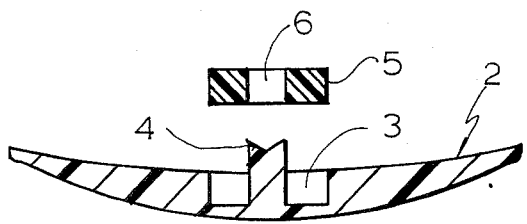
FIG. 2 is a cross-section along the line II—II in FIG. 1 before assembly of parts.
Figure 3:
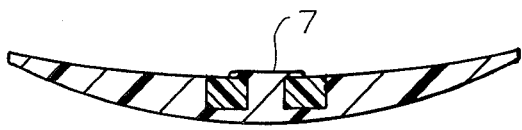
FIG. 3 is a cross-section along the line II—II in FIG. 1 after assembly of parts.
Figure 4:
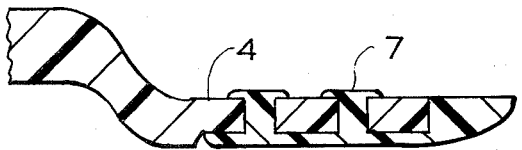
FIG. 4 is a view along the line V—V in FIG. 1.

The head plate shown in FIGS. 2 to 4 is formed with a recess 3, opening on the surface of the head plate, in which are formed two upstanding stakes, stubs, or protrusions 4. The end 5 of the hinge portion 1 is formed with two holes 6 to receive the stakes 4 and has a thickness substantially equal to the depth of the recess so that, as shown in FIGS. 3 and 4, the end 5 of the hinge portion can be received in a substantially flush manner in the recess 3. The free ends of the stakes 4 are then compressed in a press using a spinning die which both swages and welds them down onto and partly into the hinge portion, as shown at 7, thereby securing the hinge portion to the head plate.

In the modification shown in FIG. 5, the head plate is formed with a central hole 8, opening on the side of the head plate, to receive an appropriately shaped end of the hinge portion 1. If desired, adhesive or glue may be used to reinforce the connection between the head plate and the hinge portion. Other forms of fixing the head plate to the hinge portion are possible, including rivets, snap-on fixings, or adhesive fixings, provided that in each case the substantially flush fitting of the two parts is achieved.

The use of a hinge brace, as just described, is substantially the same as that of previously proposed braces. However, the arcuate cross-section of the head plate provides close conformation with a limb and this conformation, together with the elimination of dead space due to the flush connection of the head plates and hinge portion, ensure good lamination of the head plates using modern resin casting materials.

Figure 1A:
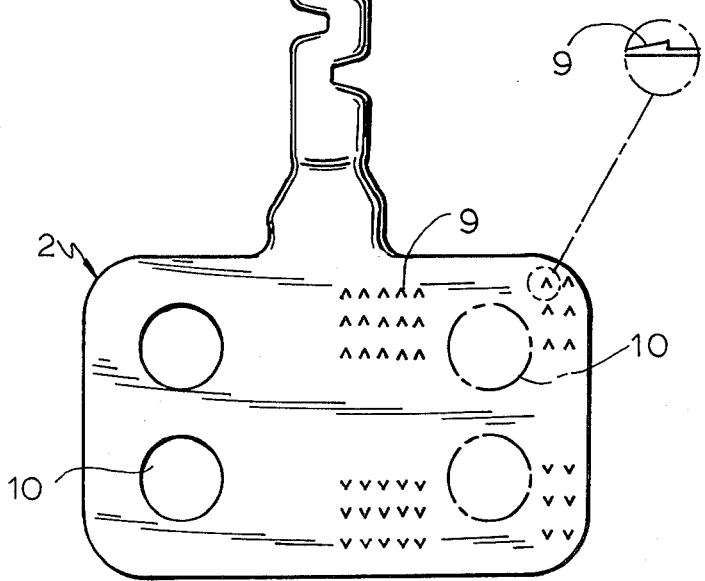

In order to improve the lamination, the head plates may be roughened or formed with teeth or splines 9 as shown at the bottom right hand side of FIG. 1 and in FIG. 1A. The teeth or splines 9 may be formed on one or both sides of the head plate and may point in any direction, or, as shown, some may point in one direction and some in another.

The head plates may be formed with holes 10 spaced from the central portion, as is conventional, but in order to enhance bonding and to reinforce the benefits of using a curved and shaped head plate, circular pieces of the casting material may be provided with the brace to fill the holes and link the underlying and overlying layers of casting fabric material.

As indicated above, a previously proposed hinge brace is in the form of a thin rectangular head plate to which the end of a hinge portion is rivetted and, thus, stands up proud above the head plate. In contradistinction, the head plate of the present hinge brace has a central portion which is at least as thick as the end of the hinge portion to enable a flush fitting arrangement of the head plate and hinge portion to be achieved, thereby eliminating dead spaces and considerably improving lamination.

The present invention makes it possible to design the head plate so that it will be thinner at its thickest central portion than the thickness of a comparable previously proposed hinge brace.

Furthermore, due to the improved lamination which can be achieved with the present hinge brace, the bond strengths which can be obtained using modern resin casting materials may equal or surpass those which can be obtained using Plaster of Paris, which may, itself, of course, be used with the present hinge brace.

The present hinge brace head plate may be formed in any suitable material, including metal, as an alternative to plastic and head plates of either material may be combined with metal monocentric or plastic polycentric hinges or with any other orthopaedic device which requires incorporation into casts. These include plastic shoe inserts, hinged ankle joint preformed fracture braces, and preformed femoral fracture bracing kits, amongst others.

While only a limited number of preferred embodiments of the present invention have been disclosed herein for purposes of illustration, it is obvious that many variations and modifications could be made thereto. It is intended to cover all of these modifications and variations which fall within the scope of the present invention, as defined by the following claims:

We claim:

1. A head plate adapted to bond to casting material for use in conjunction with a flexible hinge part having a connecting portion to form a hinge brace for a fracture cast, the head plate comprising a body with upper and lower surfaces, said body comprising a central portion with a recess of substantially the same dimensions as the hinge part connecting portion, said recess opening on one of said upper and lower surfaces, being adapted to receive the connecting portion therein with the exposed surface of the connecting portion substantially coplanar with said body surface and forming therewith a substantially continuous, uninterrupted bonding surface in said central portion of said body.

2. The head plate of claim 1, further comprising means for affixing the connecting portion within said recess.

3. The head plate of claim 2, wherein said affixing means comprises means extending from said recess and an opening in the connecting portion into which said extending means is received.

4. The head plate of claim 1, wherein said body has an arcuate cross-section.

5. The head plate of claim 1, wherein said body further comprises peripheral section and wherein said peripheral section is thinner than said central portion.

6. The head plate of claim 1, wherein said body comprises an opening spaced from the connecting portion and extending from said lower surface to said upper surface.

7. A head plate adapted to bond to casting material for use in conjunction with a flexible hinge part having a connecting portion to form a hinge brace for a fracture cast, the head plate comprising a body with upper and lower surfaces, said body comprising a central portion with a recess of substantially the same dimensions as the hinge part connecting portion, said recess opening on one of said upper and lower surfaces, being adapted to receive the connecting portion therein with the exposed surface of the connecting portion substantially coplanar with said body surface and forming therewith a substantially continuous, uninterrupted bonding surface in said central portion of said body, wherein one of said upper and lower surfaces has a rough exterior.

8. A head plate adapted to bond to casting material for use in conjunction with a flexible hinge part having a connecting portion to form a hinge brace for a fracture cast, the head plate comprising a body with upper and lower surfaces, said body comprising a central portion with a recess of substantially the same dimensions as the hinge part connecting portion, said recess opening on one of said upper and lower surfaces, being adapted to receive the connecting portion therein with the exposed surface of the connecting portion substantially coplanar with said body surface and forming therewith a substantially continuous, uninterrupted bonding surface in said central portion of said body, further comprising teeth on one of said upper and lower surfaces.

9. The head plate of claim 8, wherein said teeth form two sets and wherein said teeth of each of said sets extend in different directions.

10. A head plate adapted to bond to casting material for use in conjunction with a flexible hinge part having a connecting portion to form a hinge brace for a fracture cast, the head plate comprising a body with upper and lower surfaces, said body comprising a central portion with a recess of substantially the same dimensions as the hinge part connecting portion, said recess opening on one of said upper and lower surfaces, being adapted to receive the connecting portion therein with the exposed surface of the connecting portion substantially coplanar with said body surface and forming therewith a substantially continuous, uninterrupted bonding surface in said central portion of said body, further comprising splines on one of said upper and lower surfaces.

11. The head plate of claim 10, wherein said splines form two sets and wherein the splines in each of said sets extend in different directions.

12. A head plate adapted to bond to casting material for use in conjunction with a flexible hinge part having a connecting portion to form a hinge brace for a fracture cast, the head plate comprising a body with a central portion having substantially continuous, uninterrupted upper and lower surfaces and a side portion, a slot formed in said central portion, within the interior of said body and opening at said side portion, said slot being of substantially the same dimension as the connecting portion and adapted to receive same therein.

13. The head plate of claim 12, further comprising means for affixing the connecting portion within said slot.

14. The head plate of claim 12, wherein said body has an arcuate cross-section.

15. The head plate of claim 12, wherein said body further comprises peripheral section and wherein said peripheral section is thinner than said central portion.

16. The head plate of claim 12, wherein said body comprises an opening spaced from the connecting portion and extending from said lower surface to said upper surface.

17. The head plate of claim 12, wherein one of said upper and lower surfaces has a roughened exterior.

18. The head plate of claim 12, further comprising teeth on one of said upper and lower surfaces.

19. The head plate of claim 12, further comprising splines on one of said upper and lower surfaces.

20. The head plate of claim 18, wherein said teeth form two sets and wherein said teeth of each of said sets extend in different directions.

21. The head plate of claim 19, wherein said splines form two sets and wherein the splines in each of said sets extend in different directions.

22. A hinge brace for use in a fracture cast, the brace comprising a flexible hinge part having a head plate integrally formed on one end thereof, said head plate comprising a body with a central portion having substantially continuous uninterrupted upper and lower surfaces, said upper and lower surfaces of said central portion being substantially coplanar with the adjacent surfaces of said hinge part, respectively, said head plate having a substantially arcuate cross-section and peripheral sections located on either side of said central portion which are thinner than said central portion.

23. The head plate of claim 22, wherein said body comprises an opening spaced from the connecting portion and extending from said lower surface to said upper surface.

24. A hinge brace for use in a fracture cast, the brace comprising a flexible hinge part having a head plate integrally formed on one end thereof, said head plate comprising a body with a central portion having substantially continuous uninterrupted upper and lower surfaces, said upper and lower surfaces of said central portion being substantially coplanar with the adjacent surfaces of said hinge part, respectively, said head plate having a substantially arcuate cross-section and peripheral sections located on either side of said central portion which are thinner than said central portion, wherein one of said upper and lower surfaces has a rough exterior.

25. A hinge brace for use in a fracture cast, the brace comprising a flexible hinge part having a head plate integrally formed on one end thereof, said head plate comprising a body with a central portion having substantially continuous uninterrupted upper and lower surfaces, said upper and lower surfaces of said central portion being substantially coplanar with the adjacent surfaces of said hinge part, respectively, said head plate having a substantially arcuate cross-section and peripheral sections located on either side of said central portion which are thinner than said central portion, further comprising teeth on one of said upper and lower surfaces.

26. The head plate of claim 25, wherein said teeth form two sets and wherein said teeth of each of said sets extend in different directions.

27. A hinge brace for use in a fracture cast, the brace comprising a flexible hinge part having a head plate integrally formed on one end thereof, said head plate comprising a body with a central portion having substantially continuous uninterrupted upper and lower surfaces, said upper and lower surfaces of said central portion being substantially coplanar with the adjacent surfaces of said hinge part, respectively, said head plate having a substantially arcuate cross-section and peripheral sections located on either side of said central portion which are thinner than said central portion, further comprising splines on one of said upper and lower surfaces.

28. The head plate of claim 27, wherein said splines form two sets and wherein the splines in each of said sets extend in different directions.

29. A head plate for use with a flexible hinge part having a connecting portion of a given thickness to form a hinge brace for a fracture cast, the head plate comprising a body with a central portion having substantially continuous upper and lower surfaces, one of said surfaces defining a recess therein of substantially the same shape as the connecting portion with a depth substantially equal to the thickness of the connecting portion, and adapted to receive the connecting portion therein with the exposed surface of the connecting portion being substantially adjacent to and coplanar with the portions of said one surface proximate said recess and forming therewith a substantially continuous, uninterrupted surface for bonding with the casting material.

30. A hinge brace for use in a fracture cast, the brace comprising a flexible hinge part having a connecting portion and a head plate comprising a body with a central portion having substantially continous uninterrupted upper and lower surfaces and a side surface extending therebetween, said connecting portion extending from and being integral with said side surface, said upper and lower surfaces of said central portion being substantially coplanar with the adjacent surfaces of said connecting portion, respectively.

31. The brace of claim 30, wherein said head plate has peripheral portions on either side of said central portion and wherein said peripheral portions are thinner than said central portion.

* * * * *